US009194773B2

(12) United States Patent
Najrani

(10) Patent No.: US 9,194,773 B2
(45) Date of Patent: Nov. 24, 2015

(54) SAMPLING AND BLOCKAGE REMOVAL TOOL

(71) Applicant: Saudi Arabian Oil Company, Dhahran (SA)

(72) Inventor: Nasser Hassan Mohammed Al Najrani, Ras Tanura (SA)

(73) Assignee: Saudi Arabian Oil Company, Dhahran (SA)

(*) Notice: Subject to any disclaimer, the term of this patent is extended or adjusted under 35 U.S.C. 154(b) by 70 days.

(21) Appl. No.: 14/160,642

(22) Filed: Jan. 22, 2014

(65) Prior Publication Data
US 2015/0204762 A1    Jul. 23, 2015

(51) Int. Cl.
G01L 7/00 (2006.01)
G01N 1/20 (2006.01)
G01N 7/00 (2006.01)

(52) U.S. Cl.
CPC ............... *G01N 1/20* (2013.01); *G01N 1/2035* (2013.01); *G01N 7/00* (2013.01)

(58) Field of Classification Search
CPC ......... G01N 1/16; G01N 1/20; G01N 1/2035; G01N 2001/205
USPC ....................................................... 73/700
See application file for complete search history.

(56) References Cited

U.S. PATENT DOCUMENTS

| 3,747,411 | A | 7/1973 | McDermott et al. |
| 3,831,452 | A | 8/1974 | Pittenger |
| 4,120,313 | A | 10/1978 | Lewis |
| 4,294,124 | A | 10/1981 | Kalwaitis |
| 4,958,527 | A | 9/1990 | Couvillion |
| 6,860,162 | B1 | 3/2005 | Jaeger |
| 7,389,792 | B2 * | 6/2008 | Newberg ................ 137/551 |
| 7,886,624 | B1 | 2/2011 | Mayeaux |
| 2004/0099143 | A1 | 5/2004 | Welker |
| 2008/0098829 | A1 | 5/2008 | Nathan |

* cited by examiner

*Primary Examiner* — Lisa Caputo
*Assistant Examiner* — Roger Hernandez-Prewitt
(74) *Attorney, Agent, or Firm* — Abelman, Frayne & Schwab

(57) ABSTRACT

A sampling and blockage removal tool for mounting at a drain point of a pipeline or vessel isolation has a body, a connection valve mounted on the body and having a threaded fitting for threadably engaging in a threaded opening provided in the isolation valve of a pipeline and for securing the tool in fluid communication with the isolation valve, and a sampling tube extendable into the body. The tube is formed as hollow rod having an outer thread. A hand wheel is rotatably secured to the body without a possibility of longitudinal displacement relative thereto and has an inner thread cooperating with the outer thread of the sampling tube for longitudinally displacing the tube in opposite directions. At an end of the sampling tube remote from the body a valve structure is provided for controlling fluid flow through the sampling tube.

6 Claims, 6 Drawing Sheets

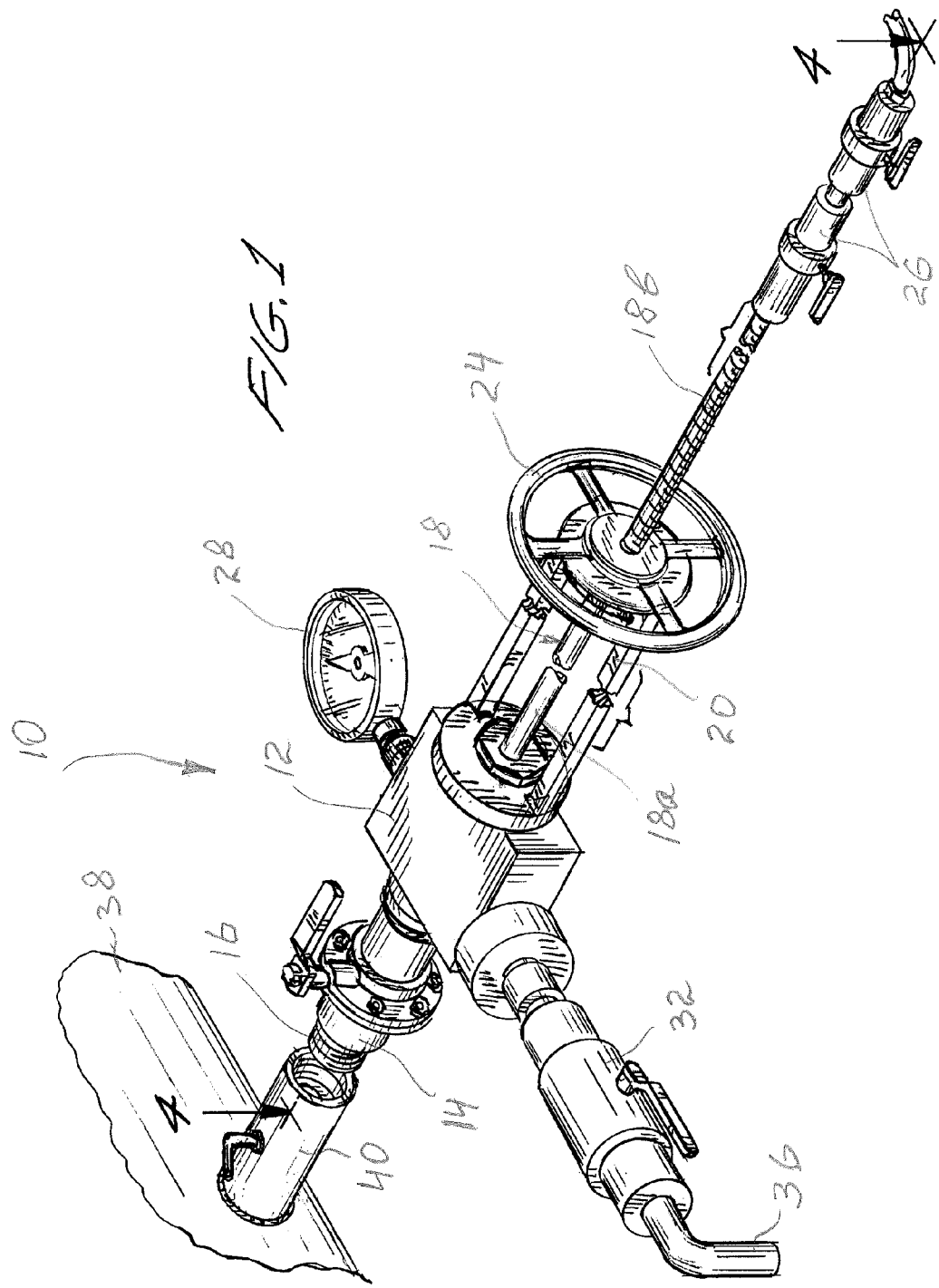

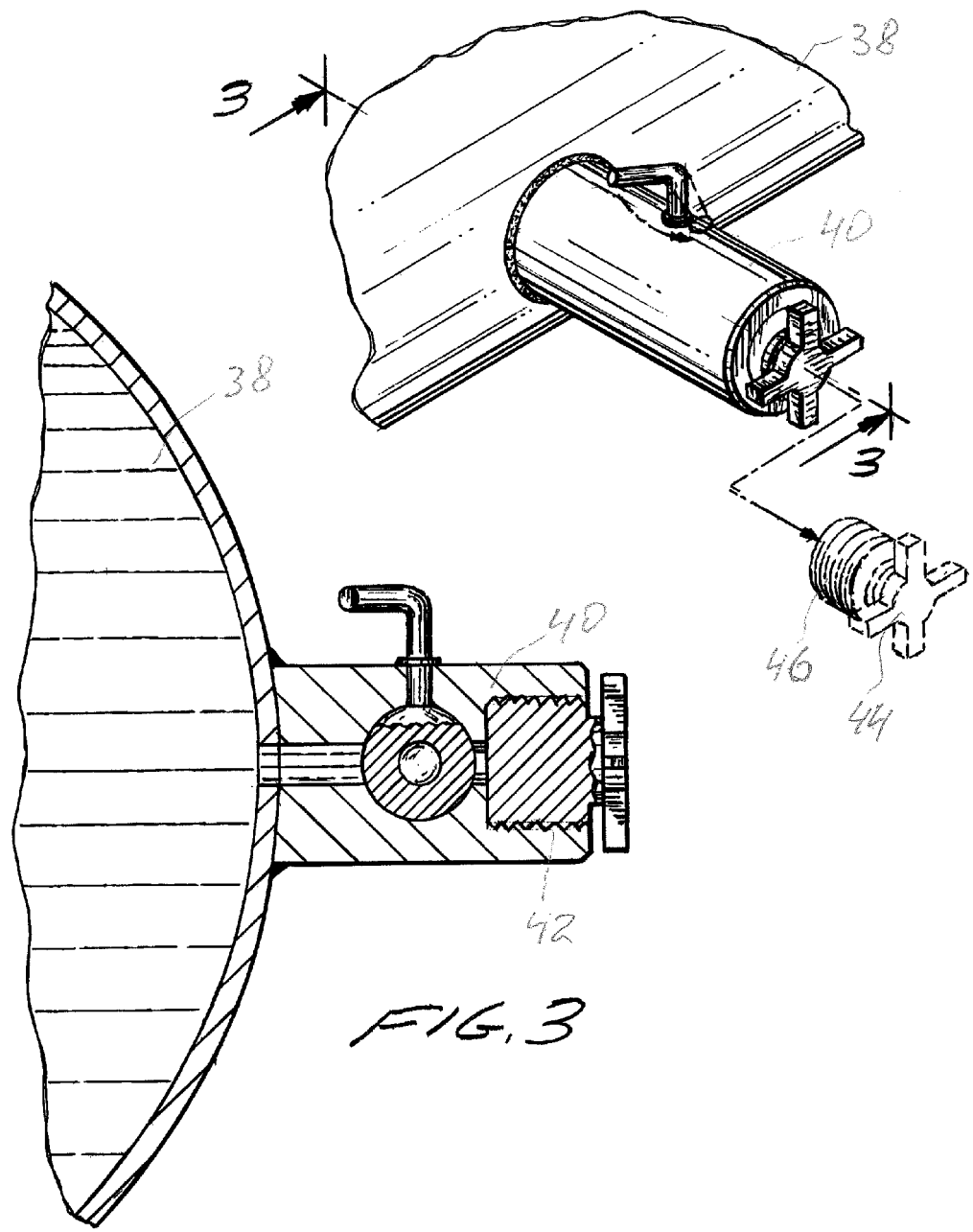

SAMPLING AND BLOCKAGE REMOVAL TOOL

BACKGROUND OF THE INVENTION

1. Field of the Invention

The present invention relates to a tool for taking fluid samples from a specific location in a pressurized vessel or a pipeline and for unplugging or removal of blockage from piping vents and drain valves.

2. Description of the Prior Art

It is frequently necessary or desirable to take samples of fluid, gas or liquid stored in pressurized vessels or flowing through a pipeline. The fluid samples are often taken from a vessel or a pipeline to obtain necessary information relating to the fluid's condition, composition and the like, e.g., fluid samples are often taken for chemical analysis. It is also desirable to be able to extract fluid samples from a specific location in the vessel or pipeline. It is further desirable to have an improved tool capable of unplugging blocked drains, vent valves, etc. It is particularly important to have such a tool in the oil industry for unplugging drains and the like without leaking of a hydrocarbon product that is contained in a vessel or flows through the pipeline, and without release of dangerous gases.

All industrial plants face a problem of removal of fluid samples because of the sample valve location for a particular pipe. Therefore, there is a need for a sampling and blockage removal tool that would permit taking samples from a desired location and in the oil industry, in particular, would prevent the danger of a sudden release of hydrocarbons in case of sludge blocking and, generally, would prevent any industrial leakage and emission of hydrocarbons or other hazardous chemicals. In this regard, the tool packing should provide reliable sealing performance.

The prior art discloses a number of different tools and apparatus for taking samples and/or inserting objects in a pipeline. Some examples follow.

U.S. Pat. No. 3,831,452 discloses a sampling device for retrieving a sample of gas in a pipeline or any desired area therein. The sampling device is securable on a ball valve mounted at a sampling port of a pipe. The device includes a housing having a sampling tube fixedly secured therein. The housing is fixedly secured to a wheel for joint displacement therewith. The wheel hub is provided with an inner thread that cooperates with a hollow threaded stem for displacing the housing together with the sampling tube along the threaded stem. The stem is provided with a threaded fitting for securing the stem in the ball valve. The sampling tube has a packing gland mounted thereon. At its end projecting from the housing, the sampling tube is provided with a thread for cooperation with a suitable valve that controls the flow of fluid through the sampling pipe.

The device has too many parts and is rather complex. Moreover, with the wheel secured to the housing, the entire structure should be displaced for advancing the sampling tube.

U.S. Pat. No. 4,120,313 discloses an apparatus for insertion of a corrosion coupon in a pipeline and removing it therefrom. The apparatus is mounted on a ball valve. The apparatus includes a cylinder and an elongate rack which is guided with the cylinder by a guide secured in the cylinder. A corrosion coupon is mounted at the operating end of the rack which is displaced by a pinion secured on the shaft attached to a handwheel. The device of the U.S. Pat. No. 4,120,313 is also very complex. Use of plurality of stems adds to the complexity of the device and a potential fluid release.

U.S. Pat. No. 4,294,124 discloses an apparatus for extraction of materials from operating vessels and including a ball valve securable to a ball valve fixedly secured at the extraction port, and an outer tube securable to the valve. An inner tube is longitudinally displaceable in the outer tube and has at its end perforations for extracting particles. A threaded rod extends into the inner tube through a threaded bore at the end of the tube remote from the ball valve. The rod is connected to a crank. The inner tube is displaceable along the rod upon rotation of the crank due to cooperation of the threaded rod with the threaded bore of tube. As in '313 patent, a plurality of stem elements add to the complexity of the device.

U.S. Pat. No. 6,860,162 discloses a device for extracting liquid fluid samples—mainly wine. The device includes a tubular probe that extends through the device body and a cylindrical plunger extending through a passage formed in the probe. The plunger moves between a first position in which the plunger tip is moved out of the passage inlet, and a second position when the passage inlet is closed. The construction of the wine sampler and, in particular the mechanism for displacing the plunger is rather complex.

A common drawback of the above-described prior art devices and methods is a comparatively complex arrangement for advancing the sampling tube. Furthermore, the known devices, because of their complexity, cannot always take a sample from a desired predetermined location.

Accordingly, an object of the present invention is to provide a sampling and blockage removal tool that solves the problem of taking a fluid sample at any predetermined location safely and reliably, while preventing any release of hazardous material into the environment.

SUMMARY OF THE INVENTION

The above-mentioned and other objects of the present invention, which will become apparent hereinafter, are achieved by providing a sampling and blockage removal tool having a body and a ball valve secured on the body and having a threaded fitting provided at a ball valve end remote from the tool body, and an elongate hollow rod extending in the tool body and having a smooth portion and a threaded portion. The tool further includes a rotatable handle attached to the tool body at the end of the body remote from the ball valve. The tool also includes a pressure gauge communicating with the body interior, and a relieve valve likewise communicating with the body interior. At the end of the hollow rod remote from ball valve, there is provided a pressure control valve. The pressure control valve is mounted on the threaded end of the hollow rod. As a pressure control valve, a double ball valve, a double plug valve, or the like can be used. Alternatively, two single ball valves, connectable with each other can be used.

The inventive sampling and blockage removal tool is used together with a conventional isolation valve or other appropriate fitting provided at a choked drain point of a pipeline. Upon attachment of the tool to the choked drain point, the threaded fitting, which is attached to the ball valve of the tool, is screwed into a threaded opening of the isolation valve which is provided at the chocked drain point. The pressure control valve, preferably, a double ball valve is connected with the collection bottle, e.g. by a flexible tube.

With the tool being mounted on the drain point and connected with the collection bottle, the drain point isolation valve and the tool connection ball valve are open, and the smooth section of the hollow rod, the end of which is located beneath the connection ball valve, is advanced into the chocked drain point by rotating the hand wheel. The free end of the rod dechocks the drain point. With the drain point being dechocked, the liquid that flows in the pipeline, enters the interior of the body. The pressure gauge, which is in communication with the body interior, registers the dechocking of the drain point. The smooth section of the rod, with the hand wheel being rotated advances further into the stream of liquid that flows in the pipeline. A clean and representative liquid sample can now be drawn into the hollow rod.

With the liquid capable to be drawn, the double ball valve or two single ball valves are open in a controlled way to provide for sample collection. The double ball valve or the valves control the fluid pressure during sampling.

After the sample has been collected, the pressure control valve is closed, the connecting flexible tube is disconnected, and the smooth section of the hollow rod is withdrawn, by rotating the hand wheel in the opposite direction, from the pipeline to the position beneath the connection ball valve.

With the smooth section of the hollow rod being withdrawn, the pipeline isolation valve and the connection ball valve are closed, and the tool is disconnected from the drain point by unscrewing the fitting which is provided on the connection ball valve. With the tool being disconnected from the drain point, the relieve valve, which also can be formed as a ball valve, is open to release the pressure from the hollow rod.

The novel features of the present invention, which are considered as characteristic for the invention, are set forth in the appended claims. The invention itself, however, both as to its construction and its mode of operation, together with additional advantages and objects thereof, will be best understood from the following detailed description of preferred embodiment, when read with reference to the accompanying drawings.

BRIEF DESCRIPTION OF THE DRAWINGS

FIG. 1 shows a perspective view of a sample extraction and blockage removal tool according to the present invention;

FIG. 2 shows a perspective view of a drain point of a pipeline;

FIG. 3 shows a cross-sectional view of a drain point of a pipeline shown in FIG. 2;

DETAILED DESCRIPTION OF THE PREFERRED EMBODIMENT

Figure 4:
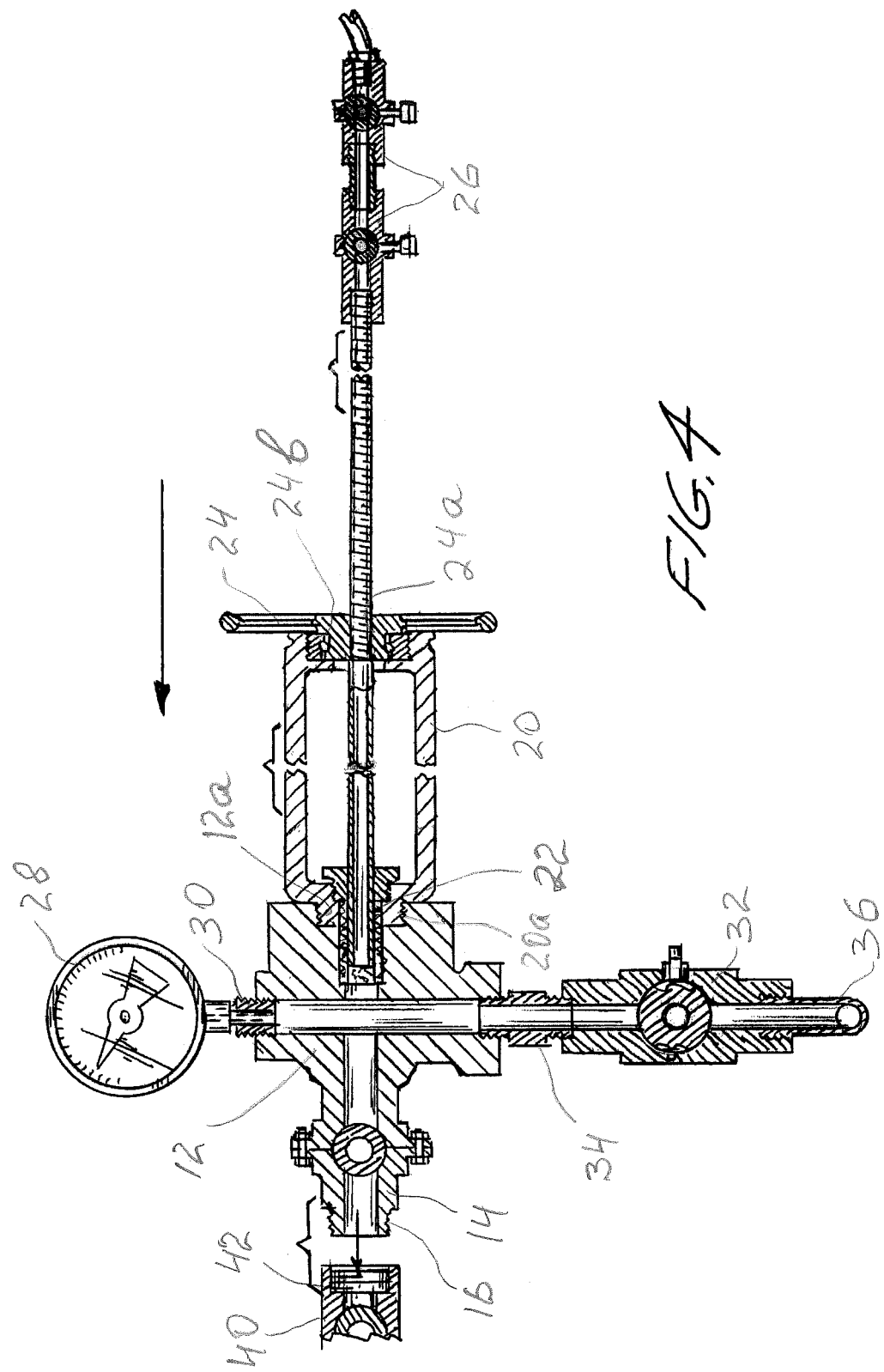
FIG. 4 shows a cross-sectional view of the tool shown in FIG. 1.
Figure 5:
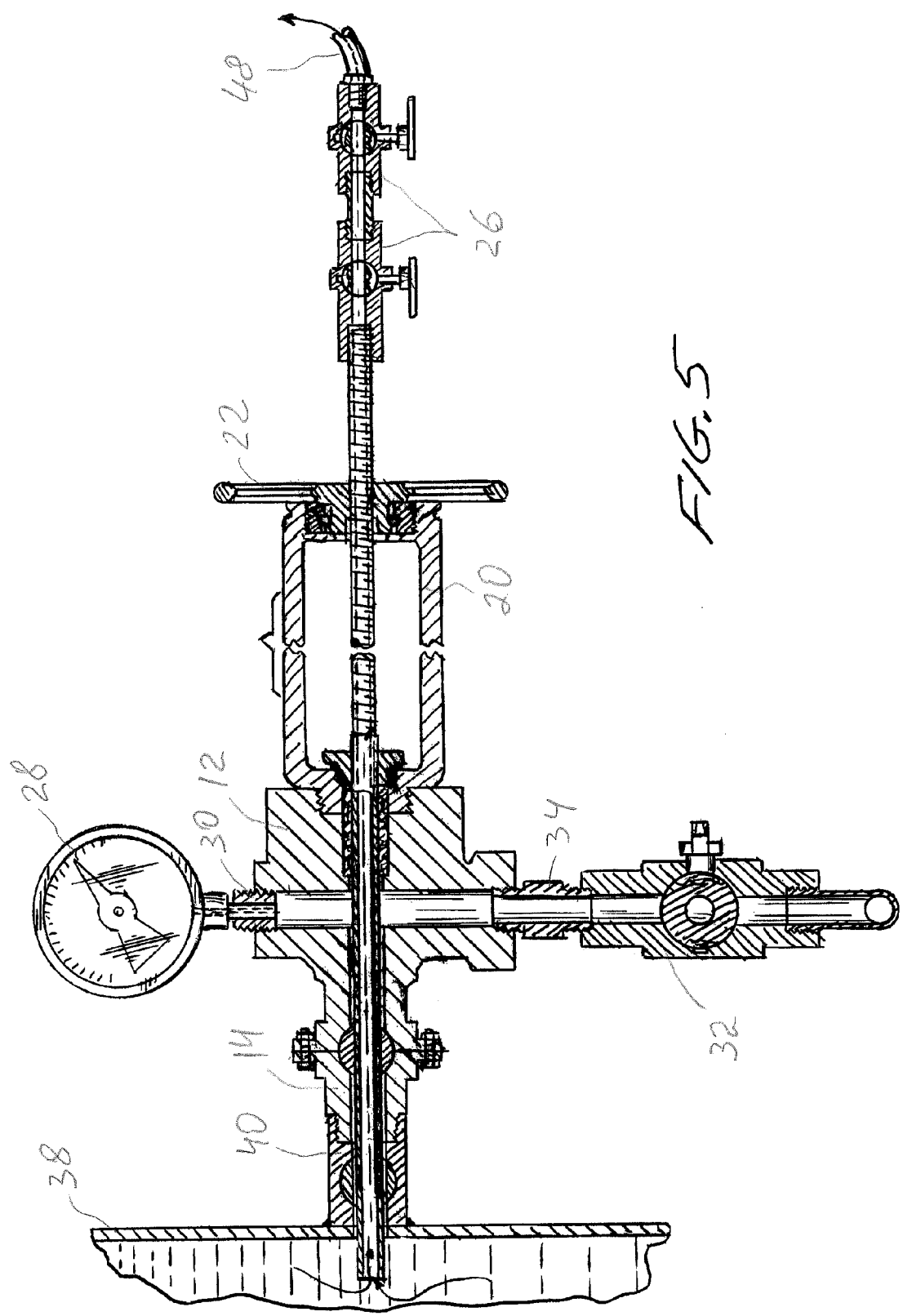
FIG. 5 shows a cross-sectional view of the inventive tool in the operational position of the tool.
Figure 6:
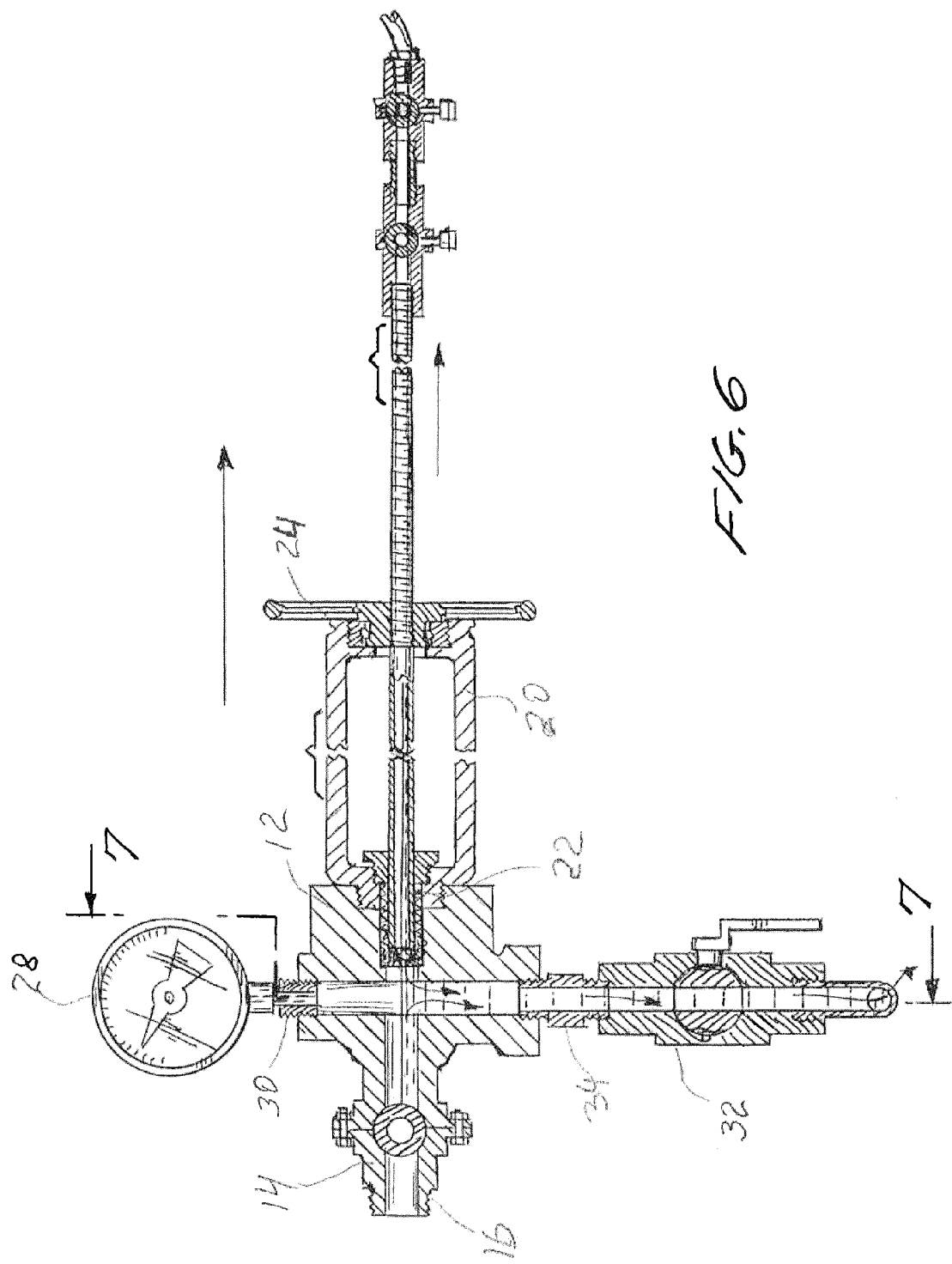
FIG. 6 shows a cross-sectional view of the inventive tool in the withdrawn position of the tool.
Figure 7:
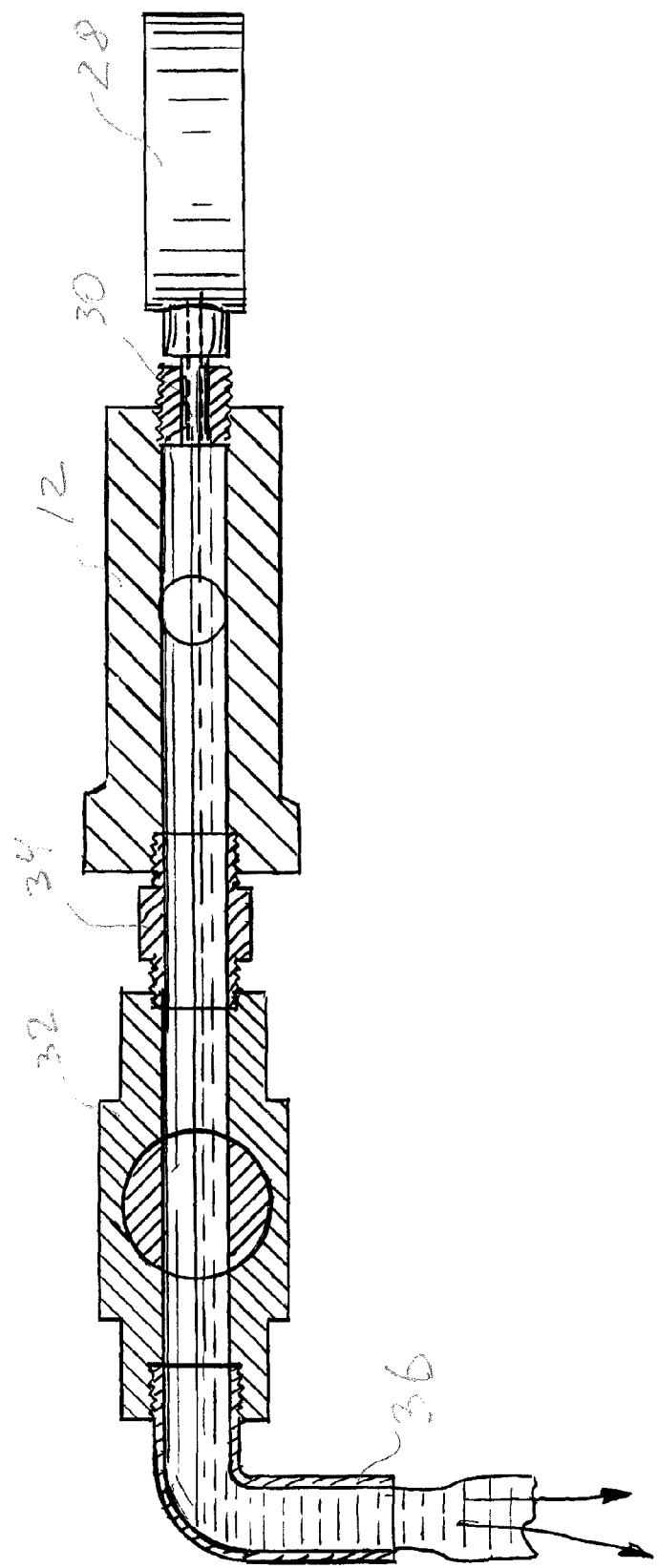
FIG. 7 shows a cross-sectional view along line 7-7 in FIG. 6.

A sampling and blockage removal tool 10 according to the present invention, which is shown in the drawings, includes a body 12 and a ball valve 14 supported on the tool body 12 and having, at its end remote from the tool body 12, a threaded fitting 16 for connecting the tool 10 to the insulation valve provided at a drain point of a pipeline through which liquid, e.g., hydrocarbon flows.

A tube that forms a sampling tube 18 extends partially through the tool body 12. The sampling tube 18 has a smooth portion 18a extending in the body 12, and a threaded portion 18b extending outside of the tool body 12. The threaded portion 18b is surrounded by a housing section 20 secured to the tool body 12 via a packaging gland 22. The housing portion 20 has a projection 20a which is threaded in a threaded opening 12a of the tool body 12. A hand wheel 24, which has a threaded bore 24a that cooperates with the threaded portion 18b for displacing the sampling tube 18 in opposite directions, is attached to the housing section 20 at the end of the housing section remote from the body 12 with a possibility of rotation relative to the housing section 20 by a bearing element 24b. At the end of the threaded section 18b, there is provided a pressure control valve, a double ball valve 26 that controls liquid pressure during sampling and connects the tool 12 with a sample collection bottle or the like.

The inventive tool further includes a pressure gauge 28 that communicates with the interior of the tool body 12, and a pressure relieve valve, preferably a ball valve 32, provided on the side of the body 12 opposite the side at which the gauge 28 is provided. Threaded tube sections 30 and 34 connect the gauge 28 and the ball valve 32 with the interior of the valve body 12, respectively. A tube 36 connects the relief valve 32 with an appropriate tank.

Below, mounting and operation of the inventive sampling and blockage removal tool 10 will be described. As discussed, the tool is designed for mounting at a drain point of a pipeline carrying liquid but can also be used for sampling a liquid stored in a vessel. By way of example, mounting of the tool at a drain point of a pipeline and the operation of the so mounted tool will be described.

For mounting of the sampling tool 10 on the pipeline 38, a plug 44, which has a threaded section 46, is screwed out of the threaded opening 42 of the isolation valve 40, and the threaded fitting 16 is screwed in the threaded opening 42 provided in the isolation valve 40 at the drain point of a pipeline 38, and the double ball valve 26 is connected, e.g., by a flexible hose 48 to a collection bottle (not shown). With the tool being so mounted, the isolation valve 40 at the drain point and the connection ball valve 14 are opened, and the sampling tube 18 is advanced into the chocked drain point by turning the hand wheel 24. With the end of the smooth portion 18a dechocking the drain point, the liquid enters the interior of the body 12 through the ball valve 14. The pressure gauge 28 measures the pressure of the liquid in the interior of the body 12. When the pressure gauge 26 indicates that a predetermined pressure, which corresponds to a complete dechocking of the drain point is reached, the smooth section 18a is advanced further into the stream of liquid, so that a clean and representative liquid sample can now be drawn through the sampling tube 18. The withdrawn liquid flows in the double ball valve 26. The ball sections of a single double ball valve or two ball valves, which are provided at the end of the threaded section 18b, are opened in a controlled manner to collect a sample.

Upon the sample being collected, the double ball valve 26 is closed, and the sampling tube 18 is retracted to its initial position, with the free end of the smooth portion 18a being clear from the bore of the ball valve 14.

The isolation valve—and the connection ball valve 14 are closed in sequence. With the connection ball valve 14 and the double ball valve 26 being closed, the relieve valve, ball valve 30 is open to release the pressure from the tool. After the pressure being released, the tool 10 is disconnected from the drain point, and is ready to be used again.

While the tool was described for opening chocked drain, it can also be used for deblocking vent valves and the like.

What is claimed is:

1. A sampling and blockage removal tool for mounting at a drain point of a pipeline or vessel having an isolation valve, the tool comprising a body; a connection valve mounted on the body and having a threaded fitting for threadably engaging in a threaded opening provided in the isolation valve of a pipeline and for securing the tool in fluid communication with the isolation valve; a sampling tube extendable into the body and formed as hollow rod having an outer thread; means rotatably secured to the body without a possibility of longitudinal displacement relative thereto and having an inner thread cooperating with the outer thread of the sampling tube for longitudinally displacing the tube in opposite directions; and means provided at an end of the sampling tube remote from the body for controlling fluid flow through the sampling tube.

2. The sampling and removal tool according to claim 1, wherein the connection valve is formed as a ball valve.

3. A sampling and removal tool according to claim 2, wherein the connection valve is formed integrally with the body.

4. A sample and removal tool according to claim 1, wherein the fluid flow control means is formed as one of double ball valve and two single ball valves connected with each other.

5. A sampling and removal tool according to claim 1, further comprising a gauge for determining fluid pressure in an interior of the body.

6. A sampling and removal tool according to claim 1, further comprising a relief valve for relieving fluid pressure in the tool.

* * * * *